(12) United States Patent
Lan et al.

(10) Patent No.: US 11,617,809 B2
(45) Date of Patent: Apr. 4, 2023

(54) INDUCTIVE COMPONENT AND UV GERMICIDAL LIGHT

(71) Applicant: SHENZHEN GUANKE TECHNOLOGIES CO., LTD, Shenzhen (CN)

(72) Inventors: Qing Lan, Shenzhen (CN); Ligen Liu, Shenzhen (CN); Shoubao Chen, Shenzhen (CN); Tianlong Dai, Shenzhen (CN); Buyuan Peng, Shenzhen (CN)

(73) Assignee: SHENZHEN GUANKE TECHNOLOGIES CO., LTD, Shenzhen (CN)

( * ) Notice: Subject to any disclaimer, the term of this patent is extended or adjusted under 35 U.S.C. 154(b) by 484 days.

(21) Appl. No.: 16/897,643

(22) Filed: Jun. 10, 2020

(65) Prior Publication Data
US 2021/0330828 A1    Oct. 28, 2021

(30) Foreign Application Priority Data
Apr. 24, 2020   (CN) .......................... 202010337831.3

(51) Int. Cl.
| | | |
|---|---|---|
| A61L 2/10 | (2006.01) | |
| G01V 3/12 | (2006.01) | |
| G01V 8/10 | (2006.01) | |

(52) U.S. Cl.
CPC .................. *A61L 2/10* (2013.01); *G01V 3/12* (2013.01); *G01V 8/10* (2013.01)

(58) Field of Classification Search
CPC .......... A61L 2/10; A61L 2/24; A61L 2202/25; A61L 2/26; A61L 9/20; A61L 2202/14; A61L 2209/11; G01V 3/12; G01V 8/10
See application file for complete search history.

(56) References Cited

U.S. PATENT DOCUMENTS

| | | | |
|---|---|---|---|
| 11,458,219 B2 * | 10/2022 | Lan | A61L 2/10 |
| 2017/0224853 A1 * | 8/2017 | Jay | A61L 2/26 |
| 2021/0403294 A1 * | 12/2021 | Szczepkowski | B66C 13/085 |

\* cited by examiner

*Primary Examiner* — David P Porta
*Assistant Examiner* — Meenakshi S Sahu
(74) *Attorney, Agent, or Firm* — Maier & Maier, PLLC (57) ABSTRACT

An inductive component and UV germicidal light. The inductive component includes: a housing and several IR sensors; the housing is provided on the lamp and is provided with one installation cavity and several mounting holes connecting the installation cavity, the several mounting holes are provided around the periphery of the shell; several IR sensors are contained in the installation cavity, each of the IR sensors is provided corresponding to one the mounting hole, the several IR sensors connect to the lamp electrically, and the IR sensors are used for sensing human bodies. The inductive component is used for sensing human bodies to work together with the lamp to turn on or turn off the lamp and improve the convenience of the lamp.

10 Claims, 5 Drawing Sheets

INDUCTIVE COMPONENT AND UV GERMICIDAL LIGHT

CROSS-REFERENCE TO RELATED APPLICATIONS

This application claims the priority of Chinese Patent Application No. 2020103378313 filed on Apr. 24, 2020, the disclosure of which is incorporated herein by reference.

FIELD

This embodiments relate to the technical field of germicidal equipment, particularly to an inductive component and a UV germicidal light using the inductive component.

BACKGROUND

In daily application, a lamp comprises a base and a luminous module setting on the base, the base connects to the luminous module electrically, and the base serves as a medium of connecting the luminous module to the base and enables the luminous module to access the power grid. Commonly, the luminous module can be used for lighting or sterilization of an environment, and when users need to turn on a lamp, they need to control the lamp with a switch or a remote control. Accordingly, artificial operation will be involved every time when users turn on or turn off a lamp, and then the lamp is frequently used. If a remote control is used for controlling the lamp, the signal receiving end of the lamp will be obstructed by the base or other articles, so the lamp will not receive signals of the remote control effectively, and then the control sensitivity is low, and it is hard to realize precise control of the lamp.

The foregoing content is only used for assisting in understanding the technical scheme of the invention, but not mean the acknowledgement of that the above content is a prior art.

SUMMARY

The main purpose of the present utility model is to provide an inductive component to enhance the usage convenience of lamps.

To achieve the afore the objective, the inductive component provided by the utility model includes:

an inductive component provided on a lamp, working together with the lamp to realize sensing of human bodies and then control the lamp to send or stop sending rays of light. the inductive component comprises:

the housing is provided on the lamp and is provided with one installation cavity and several mounting holes connecting the installation cavity, several the mounting holes are provided around the periphery of the shell; and several IR sensors are contained in the installation cavity, each of the IR sensors is provided corresponding to one the mounting hole, several the IR sensors connect to the lamp electrically, and the IR sensors are used for sensing human bodies.

In one embodiment of this utility model, the housing comprises:

a bottom shell provided on the lamp and provided with a mounting groove and a wire hole connecting the mounting groove; and upper cover connecting to the bottom shell in a dismountable way and provided with an offsetting groove and several the mounting holes going through the side wall of the offsetting groove, the notch of the offsetting groove corresponding to the notch of the mounting groove to form the installation cavity in the way of enclosure; several the IR sensors contained in the installation cavity, connecting to the upper cover and/or the bottom shell, connecting the wire hole via lead to connect with the lamp electrically.

In one embodiment of this utility model, the bottom wall of the offsetting groove is provided with several protruding locating bars, and each of the locating bars is provided nearby each of the mounting holes;

the periphery of each of the IR sensors is provided with protruding bars, each of the IR sensors passes through the mounting hole, one side of the protruding bar is against the locating bar, and the other side of the protruding bar is against the side wall of the offsetting groove respectively.

In one embodiment of this utility model, the inductive component also comprises a circuit component provided in the mounting groove and several the IR sensors provided on one side of the circuit component back on to the bottom shell and provided in a circle shape.

In one embodiment of this utility model, the inductive component also comprises a microwave sensor provided in center of the circuit component and several the IR sensors provided around the microwave sensor.

In one embodiment of this utility model, the circuit component comprises an insulation pad and a circuit board provided in the mounting groove, and the insulation pad is provided between the circuit board and the bottom shell.

In one embodiment of this utility model, the bottom wall of the mounting groove is provided with several buckling parts, the upper cover is provided with fastening parts corresponding to each of the buckling parts, each of the fastening parts can be snap-fitted with the buckle of one the buckling part to enable the upper cover to be provided on the bottom shell in a dismountable way;

and/or, the side wall of the offsetting groove is provided with at least one protruding support bar.

Wherein This utility model also provides a UV germicidal light, comprising:

the lamp whose periphery is provided with several the containing grooves provided as a reflective panel;

several UV modules provided on the lamp, contained in several the containing grooves and connecting to the lamp electrically; and the inductive component provided on the lamp and connecting to the lamp electrically;

wherein, the inductive component comprises:

the housing is provided on the lamp and is provided with one installation cavity and several mounting holes connecting the installation cavity, several the mounting holes are provided around the periphery of the shell; and several IR sensors are contained in the installation cavity, each of the IR sensors is provided corresponding to one the mounting hole, several the IR sensors connect to say lamp electrically, and the IR sensors are used for sensing human bodies.

In one embodiment of this utility model, the lamp also comprises one protective lantern ring provided around the reflex lamp housing and provided at intervals with the base to form a light access area.

The technical solution of this utility model provides several IR sensors inside the housing and takes the housing as the boosting part to provide several IR sensors on the lamp, several IR sensors connect to the lamp electrically and work together with the control circuit of the lamp to sense whether there are people in the environment, so as to control the lamp to send or stop sending light, which reduces artificial operation and improves the intelligence of the lamp; In another aspect, several IR sensors are used together to capture the environment condition and judge whether there are people in the environment to improve the detection sensitivity. In yet another aspect, several IR sensors connect to the lamp electrically, which can enhance the sensitivity of IR sensors when receiving signals of the remote control, improve the control precision and improve the usage convenience of the lamp. In yet another aspect, the housing can serve as a protective part to protect several IR sensors and reduce the damage possibility of the inductive component.

BRIEF DESCRIPTION OF THE DRAWINGS

To better describe the technical schemes of the utility model or prior art, a brief introduction of drawings to be used in the descriptions of the embodiment or prior art is made hereby. Obviously, the drawings described below are only several embodiments of the utility model. For common technicians in this field, they can obtain other drawings based on these structures shown in the drawings without making additional creative endeavors.

BRIEF DESCRIPTIONS OF MARKS IN DRAWING

| Mark No. | Name |
| --- | --- |
| 1 | Inductive component |
| 11 | Housing |
| 111 | Installation cavity |
| 112 | Mounting hole |
| 113 | Bottom shell |
| 1131 | Offsetting hole |
| 114 | Mounting groove |
| 115 | Wire hole |
| 116 | Upper cover |
| 117 | Offsetting groove |
| 118 | Locating bar |
| 1181 | The first guiding incline |
| 1182 | The second guiding incline |
| 119 | Support bar |
| 12 | Buckling part |
| 13 | Fastening part |
| 14 | IR sensor |
| 141 | Protruding bar |
| 15 | Circuit component |
| 152 | Insulation pad |
| 153 | Circuit board |
| 16 | Microwave sensor |
| 2 | Lamps |
| 21 | Containing groove |
| 22 | Lamp cap |
| 23 | Reflex lamp housing |
| 24 | Protective lantern ring |
| 25 | Light access area |
| 3 | UV module |

The implementation, functional characteristics and advantages of the utility model will be further illustrated hereinafter in conjunction with the embodiments and accompanying drawings.

DETAILED DESCRIPTION

A clear and complete description of the technical schemes combined with the drawing in utility model embodiments, this utility model embodiments clearly and completely describe the technical programs. Obviously, only some embodiments of this invention (instead of all the utility model embodiments) are described here. Based on the embodiment of the utility model, all other embodiments acquired by the common technicians in this field without creative work, shall be in the protection scope of this utility model.

It should be noted that, if there is a directional indication (upper, lower, left, right, front, and rear, etc.) in the embodiment of the utility model, the directional indication is only used to explain the relative positional relationship, motion condition, etc. between the components in a particular position (as shown in the drawing), and if the particular attitude is changed, the directional indication is changed accordingly.

In addition, if there are descriptions relating to "first", "second" and the like in embodiments of the utility model, such descriptions of "first", "second" and the like are for descriptive purposes only and are not to be construed as indicating or implying their relative importance or implying an indication of the number of indicated technical features. As such, a feature that defines as "first", "second" may explicitly or implicitly include at least one of that features. In addition, the "and/or" as stated in the whole text should be understood as there are three paralleled schemes where scheme A, or scheme B or scheme A and scheme B can be met at the same time (taking "A and/or B as an example"). In addition, the technical schemes of embodiments may be combined with each other, but must be available for common technicians in this field, and when the combination of the technical scheme is contradictory or impossible, it should be considered that the combination of the technical scheme does not exist and not fall within the scope of the utility model.

Figure 1:
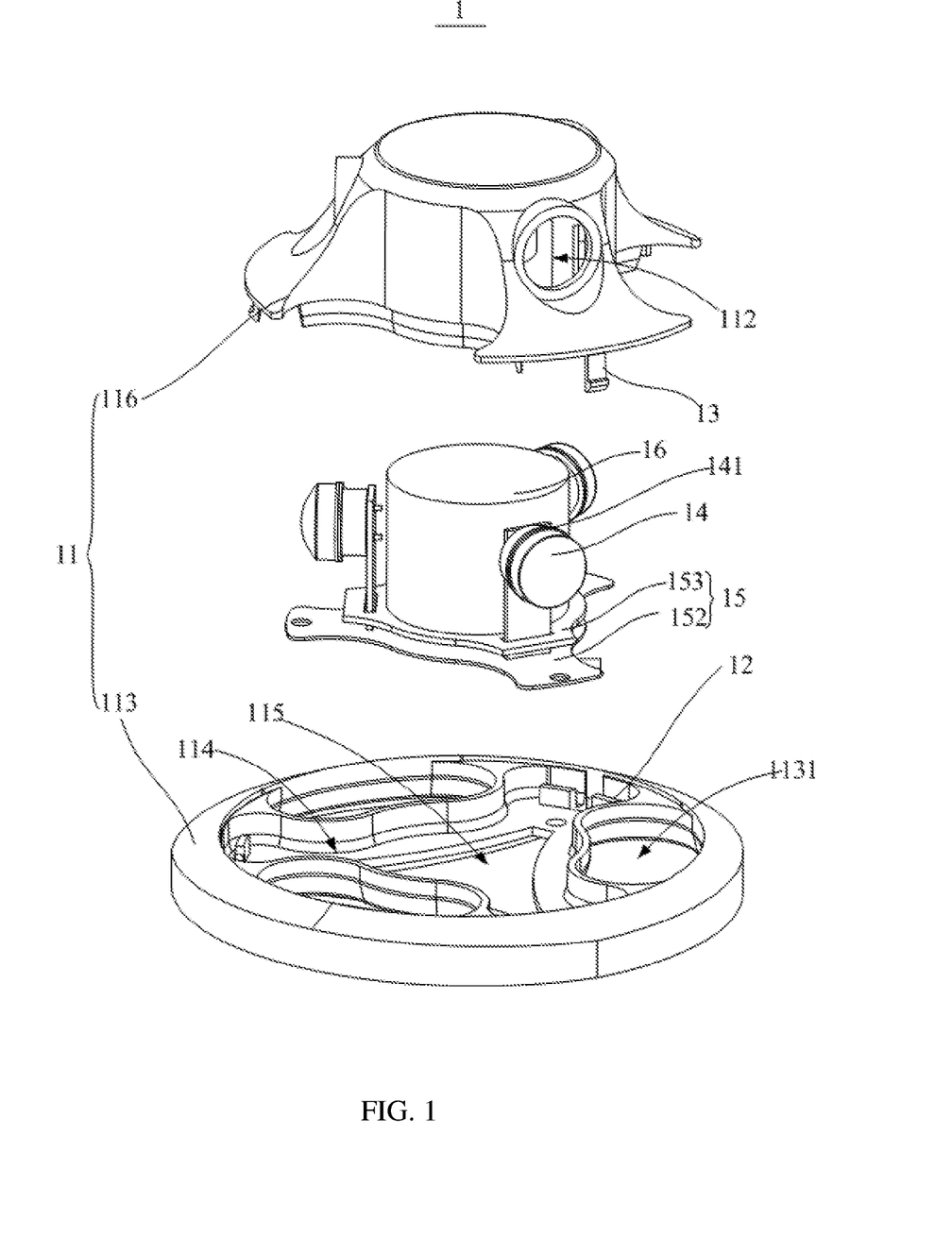
FIG. 1 is a schematic diagram showing the assembly structure of an embodiment of inductive component of this utility model.
Figure 2:
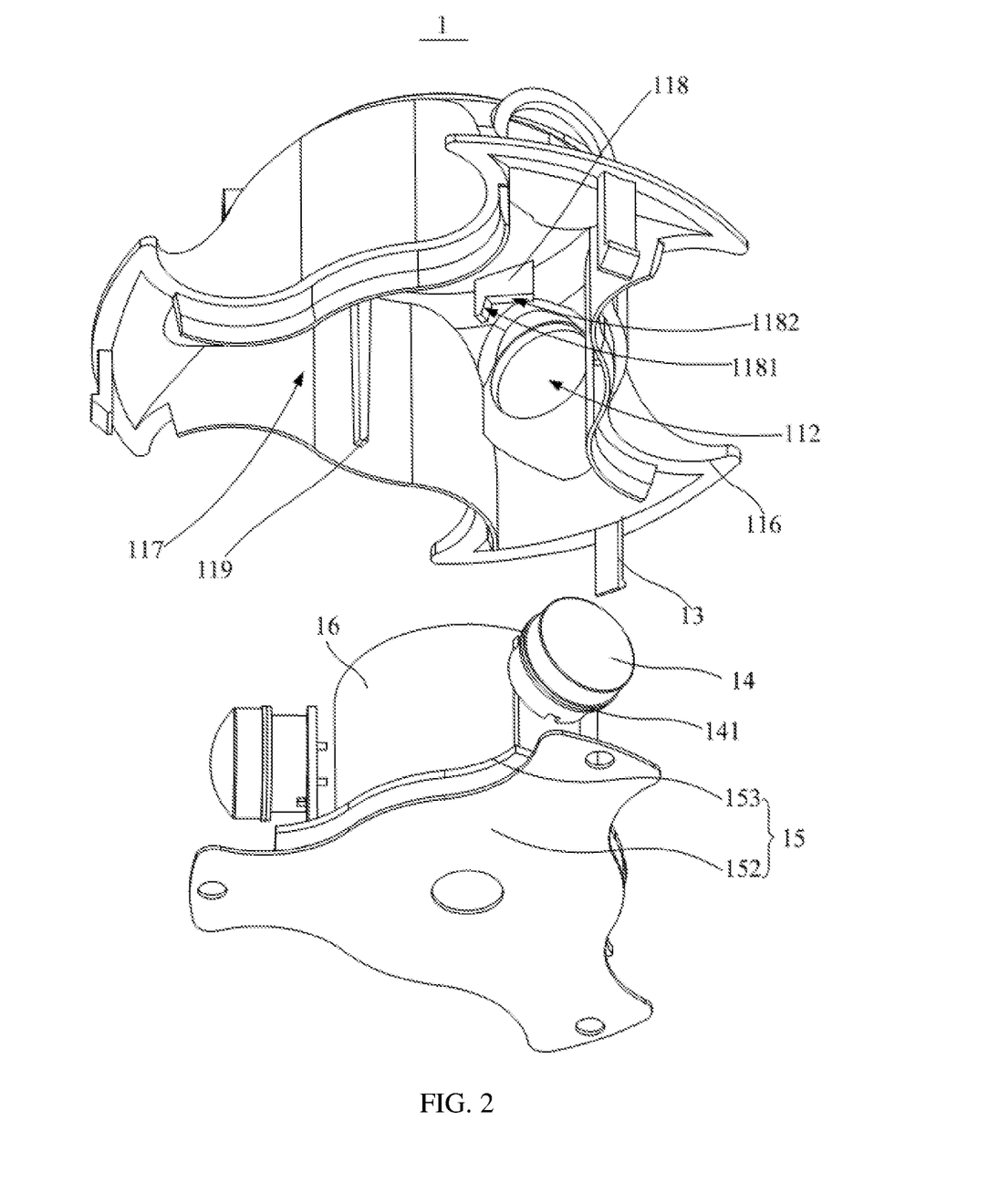
FIG. 2 is a schematic diagram showing the structure of inductive component in FIG. 1.
Figure 3:
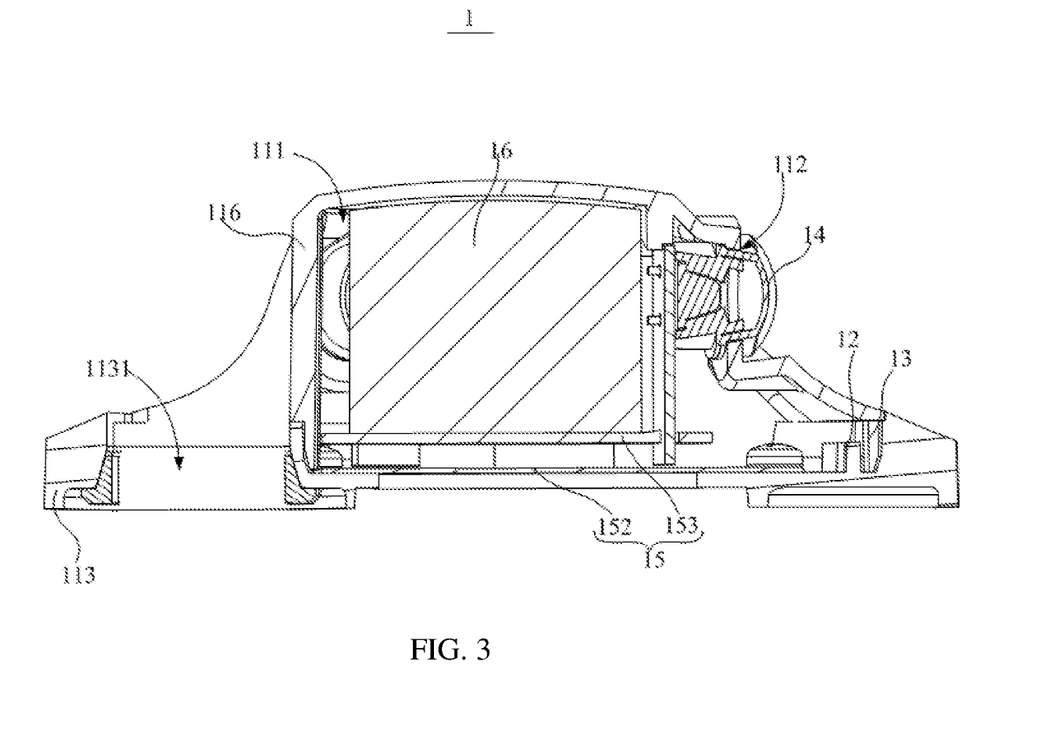
FIG. 3 is a schematic diagram showing the cross-sectional structure of inductive component in FIG. 1.
Figure 4:
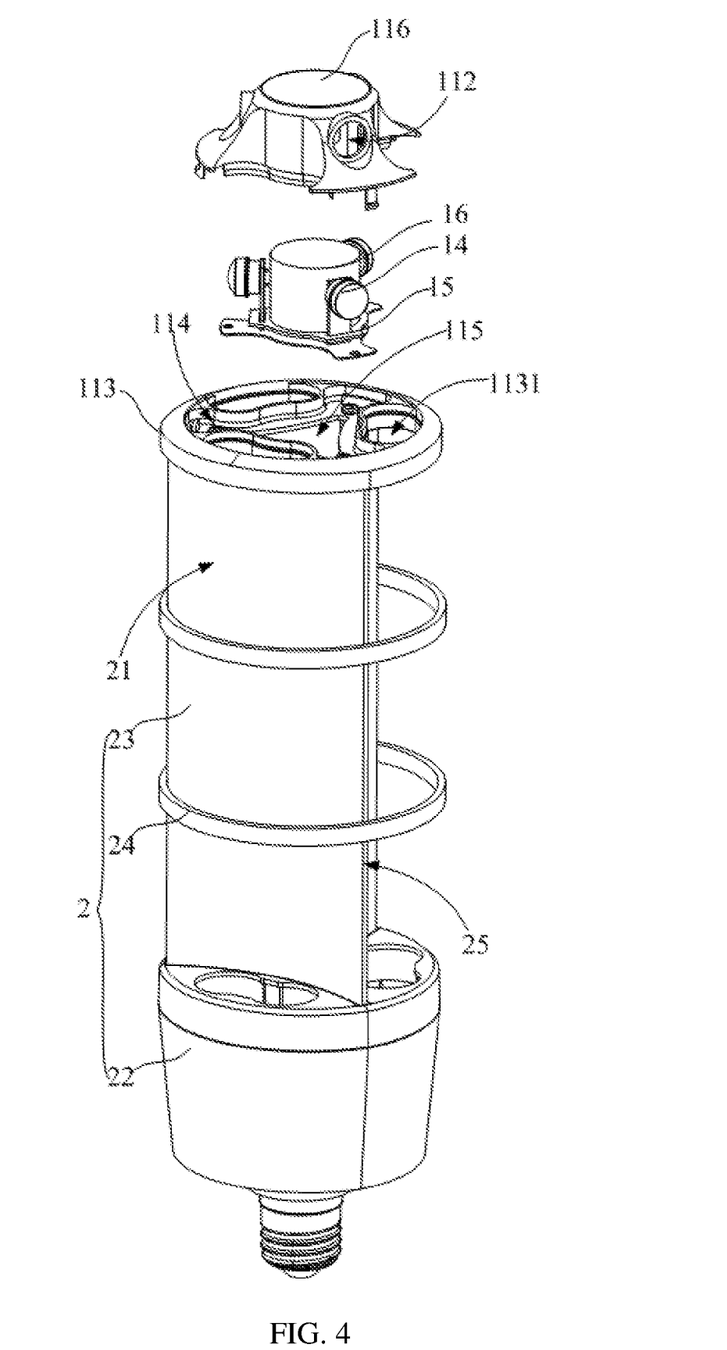
FIG. 4 is a schematic diagram showing the structure of UV germicidal light of this utility model.
Figure 5:
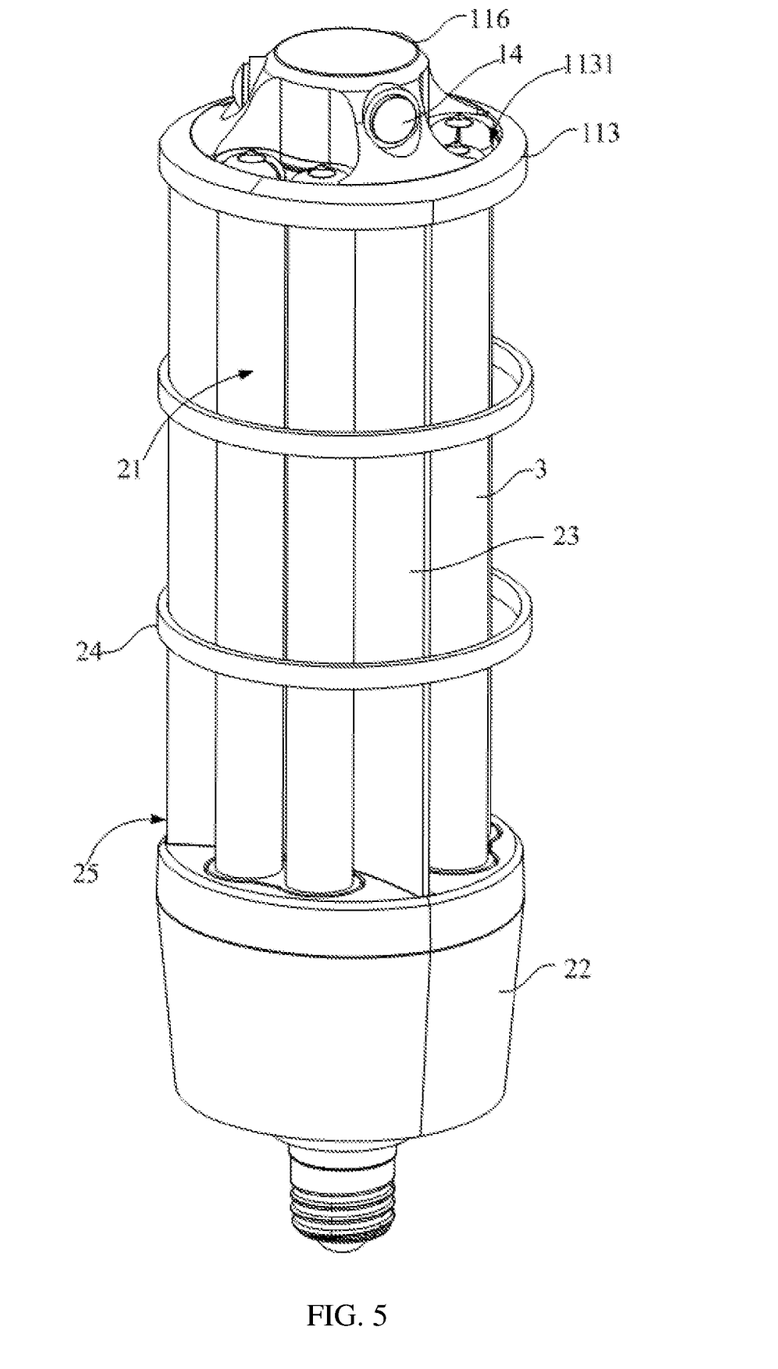
FIG. 5 is another schematic diagram showing the structure of UV germicidal light in FIG. 4.

This utility model provides an inductive component provided on a lamp, working together with the lamp to realize sensing of human bodies and then control the lamp to send or stop sending rays of light. Refer to FIG. 1, it is a schematic diagram showing the assembly structure of an embodiment of inductive component of this utility model; Refer to FIG. 2, it is a schematic diagram showing the structure of inductive component in FIG. 1; Refer to FIG. 3, it is a schematic diagram showing the cross-sectional structure of inductive component in FIG. 1; Refer to FIG. 4, it is a schematic diagram showing the structure of UV germicidal light of this utility model; Refer to FIG. 5, it is another schematic diagram showing the structure of UV germicidal light in FIG. 4.

In the embodiment of this utility model, as shown in FIG. 1 and according to FIG. 2, FIG. 3 and FIG. 4, the inductive component 1 comprises housing 11 and several IR sensors 14; wherein, housing 11 is provided on lamp 2, housing 11 is provided with an installation cavity 111 and several mounting holes 112 connecting installation cavity 111, and several mounting holes 112 are provided around the periphery of housing 11; several IR sensors 14 are contained in installation cavity 111, each of IR sensors 14 is provided corresponding to a mounting hole 112, several IR sensors 14 connect to lamp 2, and IR sensor 14 are used for sensing human bodies.

In this embodiment, this utility model provides several IR sensors 14 inside the housing 11 and takes the housing 11 as the boosting part to provide several IR sensors 14 on the lamp 2, several IR sensors 14 connect to the lamp 2 electrically and work together with the control circuit of the lamp 2 to sense whether there are people in the environment, so as to control the lamp 2 to send or stop sending light, which reduces artificial operation and improves the intelligence of the lamp 2; In another aspect, several IR sensors 14 are used together to capture the environment condition and judge whether there are people in the environment to improve the detection sensitivity. In yet another aspect, several IR sensors 14 connect to the lamp 2 electrically, which can enhance the sensitivity of IR sensors when receiving signals of the remote control, improve the control precision and improve the usage convenience of the lamp 2. In yet another aspect, the housing 11 can serve as a protective part to protect several IR sensors 14 and reduce the damage possibility of the inductive component 1.

Optionally, IR sensor 14 is regular model, and the specific model is not restricted here.

Optionally, IR sensor 14 can be fixed to housing 11 with adhesive; or, a clamping structure can be set on housing 11 to clamp IR sensor 14 to housing 11 in a dismountable way, for which there is no restriction description.

In specific application of this embodiment, lamp 2 is provided with a luminous module which can be illuminating tube or UV fluorescent tube.

For UV fluorescent tube serving as the luminous module, to improve the usage convenience of lamp 2, when inductive component 1 senses approaching human bodies, inductive component 1 will control the UV fluorescent tube to stop working; When inductive component 1 does not sense human bodies, and there are no people in the surrounding environment, inductive component 1 will control UV fluorescent tube to start to work. In another aspect, a certain working duration of lamp 2 can be preset, that is, user can set the processing time of lamp 2, and UV fluorescent tube carries out sterilization and disinfection within a period of time. Wherein, the working time value can be any value, such as: 30 min, 60 min, 90 min and 120 min, etc.

For illuminating tube serving as the luminous module, in a dark environment where people cannot see the road or things clearly, to improve the usage convenience of illuminating tube, when inductive component 1 senses approaching human bodies, the illuminating tube will start to work; When inductive component 1 does not sense human bodies, and there are no people in the surrounding environment, inductive component 1 will control illuminating tube to stop working.

In one embodiment of this utility model, according to FIG. 1, FIG. 2 and FIG. 3, housing 11 comprises:

bottom shell 113 provided on lamp 2 and provided with mounting groove 114 and wire hole 115 connecting mounting groove 114; and upper cover 116 connecting to bottom shell 113 in a dismountable way, provided with offsetting groove 117 and several mounting holes 112 connecting the side wall of offsetting groove 117 whose notch is corresponding to the notch of mounting groove 114, to form an installation cavity 111 in the way of enclosure;

several IR sensors 14 contained in installation cavity 111, connecting to upper cover 116 and/or bottom shell 113, and connecting to lamp 2 electrically via lead connecting wire hole 115.

In this embodiment, bottom shell 113 and upper cover 116 combine to cover several IR sensors 14 to protect IR sensor 14.

Optionally, IR sensor 14 can be provided on bottom shell 113 and corresponding to mounting hole 112 of upper cover 116.

Optionally, IR sensor 14 can be provided on upper cover 116 and corresponding to mounting hole 112 of upper cover 116.

In one embodiment of this utility model, according to FIG. 2, the bottom wall of offsetting groove 117 is provided with several protruding locating bars 118, and each of locating bars 118 is provided nearby each of mounting holes 112;

the periphery of each of IR sensors 14 is provided with protruding bar 141, each of IR sensors 14 passes through mounting hole 112, one side of protruding bar 141 is against locating bar 118 and the other side of protruding bar 141 is against the side wall of offsetting groove 117.

In this embodiment, upper cover 116 is provided with locating bar 118, the periphery of each of IR sensors 14 is provided with protruding bar 141, locating bar 118 and the inner wall of offsetting groove 117 form a certain space; when IR sensor 14 is provided in mounting hole 112, protruding bar 141 on the periphery of IR sensor 14 is just clamped between locating bar 118 and the inner wall of offsetting groove 117 to further locate IR sensor 14.

Optionally, protruding bar 141 can be made of elastic or plastic materials, such as plastic or silica gel.

Optionally, according to FIG. 2, the end of locating bar 118 away from the bottom wall of offsetting groove 117 is provided with the first guiding incline 1181 and the second guiding incline 1182, the first guiding incline 1181 and the second guiding incline 1182 are provided by leaving an included angle and are used for guiding IR sensor 14. In other words, when installing IR sensor 14 into mounting hole 112, the periphery of IR sensor 14 can move under the guidance of the first guiding incline 1181 and/or the second guiding incline 1182 to make IR sensor 14 passes through mounting hole 112, realizing fast installation of IR sensor 14; In another aspect, after IR sensor 14 is installed into mounting hole 112, IR sensor 14 can also be located between the first guiding incline 1181 and the second guiding incline 1182 to further locate IR sensor 14.

Optionally, the included angle between the first guiding incline 1181 and the second guiding incline 1182 is less than 180°.

In one embodiment of this utility model, inductive component 1 also comprises circuit component 15 provided in mounting groove 114, several IR sensors 14 are provided on one side of circuit component 15 back on to bottom shell 113 and provided in a circle shape.

In this embodiment, several IR sensors 14 are provided on circuit component 15 which serves as a carrier to make several IR sensors 14 be provided on circuit component 15 steadily and be installed in installation cavity 111 steadily. Wherein, circuit component 15 can comprise printed circuit board 153. In another aspect, several IR sensors 14 are provided in a circle shape to effectively capture environment information within the scope of 360° of the periphery of the inductive component to determine whether there are people.

In one embodiment of this utility model, according to FIG. 2, inductive component 1 also comprises microwave sensor 16 provided in the center of circuit component 15, and several IR sensors 14 are provided around microwave sensor 16.

In this embodiment, on the basis of several IR sensors 14, microwave sensor 16 is provided to sense whether there are people in the environment in the way of microwave to further judge accurately where there are people in the environment and improve the sensitivity of inductive component 1. In another aspect, several IR sensors 14 are provided around microwave sensor 16 whose microwave receiving & sending end is vertical to the IR acquisition end of several IR sensors 14 to avoid mutual obstruction and improve the working stability of inductive component 1.

In one embodiment of this utility model, according to FIG. 1, FIG. 2 and FIG. 3, circuit component 15 comprises insulation pad 152 and circuit board 153 provided in mounting groove 114, and insulation pad 152 is provided between circuit board 153 and bottom shell 113.

In this embodiment, bottom shell 113 is made of metal or plastic, which can be determined according to the actual production need. When bottom shell 113 is metal, if circuit board 153 directly adheres to bottom shell 113, short circuit is likely to happen to components of circuit board 153, and accordingly, insulation pad 152 is provided between circuit board 153 and bottom shell 113 to realize insulation between circuit board 153 and bottom shell 113 to protect circuit board 153 and improve the working stability of inductive component 1.

Wherein, insulation pad 152 can be plastic or silica gel.

In one embodiment of this utility model, according to FIG. 1 and FIG. 2, the bottom wall of mounting groove 114 is provided with buckling part 12, upper cover 116 is provided with fastening part 13 corresponding to each of buckling parts 12, each of fastening parts 13 is snap-fitted with each of buckling parts 12 to make upper cove 116 be provided on bottom shell 113 in a dismountable way.

In this embodiment, each of fastening parts 13 can be snap-fitted with each of buckling parts 12 to make upper cover 116 be provided on bottom shell 113 in a dismountable way to realize a dismountable connection structure between upper cover 116 and bottom shell 113 to facilitate disassembly & assembly and maintenance of inductive component 1.

Optionally, fastening part 13 can be a buckle, and buckling part 12 can be a clamping slot.

Optionally, the bottom wall of mounting groove 114 can be provided with several protruding locating bars (not shown in the drawing), several locating bars and the side wall of mounting groove 114 are provided at intervals to form several buckling parts 12.

In one embodiment of this utility model, according to FIG. 2, the side wall of offsetting groove 117 is provided with at least one protruding support bar 119 to enhance the structural strength of upper cover 116. In another aspect, when bottom shell 113 and upper cover 116 connect, one end of support bar 119 nearby bottom shell 113 can be against circuit board 153 to locate circuit board 153.

This utility model also provides a UV germicidal light. According to FIG. 4 and FIG. 5, the UV germicidal light comprises lamp 2, several UV modules 3 and inductive component 1. See the specific structure of the inductive component 1 in the above embodiment. Since the UV germicidal light adopts all the technical solutions of all the afore the embodiments, at least the UV germicidal light can achieve all the beneficial effects of all the technical solutions of afore the embodiments, so unnecessary details will not be given here. Wherein, the periphery of lamp 2 is provided with several containing grooves 21 which are provided as a reflective panel; several UV modules 3 are provided on lamp 2 and are contained in several containing grooves 21, and several UV modules 3 connect to lamp 2 electrically; inductive component 1 is provided on lamp 2 and connect to lamp 2 electrically;

Optionally, UV module 3 can be UV fluorescent tube or LED UV lamp, for which there is no restriction description here.

In one embodiment of this utility model, according to FIG. 4 and FIG. 5, lamp 2 comprises lamp cap 22 and reflex lamp housing 23, reflex lamp housing 23 is provided outside lamp cap 22, and the periphery of reflex lamp housing 23 is provided with several containing grooves 21; several UV modules 3 connect to lamp cap 22 and are contained in several containing grooves 21.

In this embodiment, reflex lamp housing 234 is provided around lamp cap 22, the periphery of reflex lamp housing 234 is provided with several containing grooves 21, and the inner wall of each of containing grooves 21 is provided as a reflective panel; wherein, several UV modules 3 are provided on lamp cap 22, connect to lamp cap 22 electrically, and are contained in several containing grooves 21, taking lamp cap 22 as the connection base of connecting the power, lamp cap 22 can provide supply for several UV modules 3, and several UV modules 3 in several containing grooves 21 send ultraviolet rays. Understandably, reflex lamp housing 23 is provided outside lamp cap 22 in a protruding way to reduce the possibility of radiating ultraviolet rays onto lamp cap 22; in another aspect, several UV modules 3 send ultraviolet rays to enhance UV illumination within the unit time and enhance the coverage of rays of light, improve the UV sterilization efficiency and reduce UV sterilization time; in yet another aspect, several containing grooves 21 on the periphery of reflex lamp housing 23 are provided as a reflective panel, so that after several UV modules 3 send ultraviolet rays, ultraviolet rays can be reflected by the inner wall of containing groove 21 of reflex lamp housing 23 to the environment to realize that the environment around lamp cap 22 can be illuminated by ultraviolet rays, illumination of ultraviolet rays is improved, and the sterilization effect is improved.

Understandably, lamp cap 22 can be provided with a control circuit (not shown in the drawing), the control circuit connects to several IR sensors 14 of inductive component 1 electrically to determine whether there are people in the environment.

In one embodiment of this utility model, lamp 2 also comprises at least one protective lantern ring 24 provided around reflex lamp housing 23, and protective lantern ring 24 and the base are provided at intervals to form a light access area 25.

In one embodiment of this utility model, lamp 2 also comprises several protective lantern rings 24 provided along the length of reflex lamp housing 23, and two neighboring protective lantern rings 24 are provided at intervals.

In this embodiment, protective lantern ring 24 is provided around reflex lamp housing 23, the periphery of reflex lamp housing 23 is provided with several containing grooves 21, so that protective lantern ring 24 can span the notch of several containing grooves 21 and protective lantern ring 24 can partially cover the notch of containing groove 21; In other words, protective lantern ring 24 serves as a shielding thing to effectively protect UV module 3 from collision of external articles.

In one embodiment of this utility model, bottom shell 113 can be provided with offsetting hole 1131 corresponding each of UV modules 3, and one end of each of UV modules 3 away from lamp cap 22 passes through offsetting hole 1131.

In one embodiment of this utility model, the inner wall of the offsetting hole 1131 can be provided with an elastic washer which serves as a buffering part, the elastic washer can be provided between UV module 3 and the inner wall of offsetting hole 1131.

the description is only the preferred embodiment of the utility model, and it is not for this reason that the patent scope of the utility model is limited. Any equivalent structural transformation made by using the description of the utility model and the drawing, or direct/indirect application in other related innovation technical fields under the inventive concept of the utility model, is included in the patent protection scope of the utility model.

What is claimed is:

1. An inductive component provided on a lamp, comprising:
   a housing is provided on the lamp and further provided with one installation cavity and a plurality of mounting holes connecting the installation cavity, the plurality of mounting holes are provided around the periphery of the shell; and
   a plurality of IR sensors are contained in the installation cavity, each of the IR sensors is provided corresponding to one of the plurality of mounting holes, the plurality of IR sensors connect to say lamp electrically, and the plurality of IR sensors are used for sensing human bodies.

2. The inductive component as claimed in claim 1, wherein the housing comprises:
   a bottom shell provided on the lamp and provided with a mounting groove and a wire hole connecting the mounting groove; and
   an upper cover connecting to the bottom shell in a dismountable way and provided with an offsetting groove and the plurality of mounting holes going through a side wall of the offsetting groove, a notch of the offsetting groove corresponding to a notch of the mounting groove to form the installation cavity in the way of enclosure;
   the plurality of IR sensors contained in the installation cavity, connecting to the upper cover and/or the bottom shell, connecting a wire hole via a lead to connect with the lamp electrically.

3. The inductive component as claimed in claim 2, wherein a bottom wall of the offsetting groove is provided with several protruding locating bars, and each of the locating bars is provided nearby each of the mounting holes;
   a periphery of each of the plurality of IR sensors is provided with protruding bars, each of the IR sensors passes through the mounting hole, one side of the protruding bar is against the locating bar, and the other side of the protruding bar is against the side wall of the offsetting groove respectively.

4. The inductive component as claimed in claim 2, wherein the inductive component also comprises a circuit component provided in the mounting groove and the plurality of IR sensors provided on one side of the circuit component back on to the bottom shell and provided in a circle shape.

5. The inductive component as claimed in claim 4, wherein the inductive component further comprises a microwave sensor provided in center of the circuit component and the plurality of IR sensors provided around the microwave sensor.

6. The inductive component as claimed in claim 4, wherein the circuit component comprises an insulation pad and a circuit board provided in the mounting groove, and the insulation pad is provided between the circuit board and the bottom shell.

7. The inductive component as claimed in claim 2, wherein the bottom wall of the mounting groove is provided with several buckling parts, the upper cover is provided with fastening parts corresponding to each of the buckling parts, each of the fastening parts can be snap-fitted with the buckle of one the buckling part to enable the upper cover to be provided on the bottom shell in a dismountable way;
   and/or, the side wall of the offsetting groove is provided with at least one protruding support bar.

8. A UV germicidal light, which comprising:
   a lamp whose periphery is provided with a plurality of containing grooves provided as a reflective panel;
   a plurality of UV modules provided on the lamp, contained in several the containing grooves and connecting to the lamp electrically; and
   the inductive component of claim 1, provided in the lamp and connecting to the lamp electrically.

9. The UV germicidal light as claimed in claim 8, wherein the lamp comprises a lamp cap and a reflex lamp housing, the reflex lamp housing is provided by covering the lamp cap, and the periphery of the reflex lamp housing is provided with a plurality of containing grooves;
   the plurality of UV modules connect to the lamp cap and are contained in the plurality of containing grooves.

10. The UV germicidal light as claimed in claim 8, wherein the lamp further comprises at least one protective lantern ring provided around the reflex lamp housing and provided at intervals with the base to form a light access area.

* * * * *